United States Patent [19]

Hancock

[11] 4,397,759
[45] Aug. 9, 1983

[54] FIRE RETARDANT FOR POLYOLEFINS

[76] Inventor: Henry Hancock, 5 Laurel Trail, Kinnelon, N.J. 07405

[21] Appl. No.: 60,661

[22] Filed: Jul. 25, 1979

Related U.S. Application Data

[63] Continuation of Ser. No. 903,201, May 5, 1978, abandoned, which is a continuation-in-part of Ser. No. 829,890, Sep. 1, 1977, Pat. No. 4,139,476.

[51] Int. Cl.³ .......................... C09K 3/28; C09D 5/18
[52] U.S. Cl. .............................. 252/609; 106/18.18; 428/921; 524/117; 524/119
[58] Field of Search ................ 106/20, 18.18; 8/DIG. 9; 252/8.1, 609; 260/45.8 R, 927 R, 937, 969

[56] References Cited

U.S. PATENT DOCUMENTS

| | | | |
|---|---|---|---|
| 3,789,091 | 1/1974 | Anderson et al. | 260/927 R |
| 3,849,368 | 11/1974 | Anderson et al. | 260/45.8 R |
| 3,978,166 | 8/1976 | Hechenbleikner | 428/921 X |
| 4,001,367 | 1/1977 | Guthrie et al. | 106/18.15 |
| 4,055,702 | 10/1977 | Guthrie et al. | 428/921 X |
| 4,139,476 | 2/1979 | Hancock | 252/8.1 |

*Primary Examiner*—Richard D. Lovering
*Attorney, Agent, or Firm*—Stephen E. Feldman; Marvin Feldman; Jules L. Chaboty

[57] ABSTRACT

Polypropylene and other polyolefins are rendered flame retardant by the addition of a phosphonate ester having the following formula:

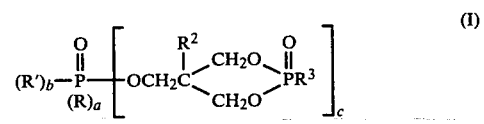

(I)

wherein a 0, 1 or 2, b is 0, 1 or 2, c is 1, 2 or 3 and a+b+c is 3; R and R' are the same or dissimilar and are alkyl, alkoxy, aryl, aryloxy, alkaryl, alkaryloxy, aralkyl, aryloyxalkoxy, or aralkoxy; wherein the alkyl portion of these groups may contain hydroxyl but no halogen and the aryl portion may contain chlorine bromine and hydroxyl groups; $R^2$ is alkyl, hydroxyalkyl, or aryl; $R^3$ is lower alkyl ($C_1$–$C_4$); and a wetting agent penetrant. The presence of the penetrant promotes penetration of the retardant composition into the polypropylene. This fire retardant composition is particularly useful in polypropylene fibers and fabrics particularly where the fibers are woven into a matte.

5 Claims, No Drawings

FIRE RETARDANT FOR POLYOLEFINS

This is a continuation of Ser. No. 903,201, filed May 5, 1978, now abandoned, which is a continuation-in-part of Ser. No. 829,890, filed Sept. 1, 1977, now U.S. Pat. No. 4,139,476, issued on Feb. 13, 1979.

FIELD OF THE INVENTION

This invention relates to a fire retardant composition for polyolefins. Specifically this invention relates to providing a fire retardant polyolefin.

DESCRIPTION OF THE PRIOR ART

Flame retardancy has become a major consideration for many plastic articles used in industrial, commercial and household products. The poly-α-olefins have been, and are being considered in these areas specifically in the textile area where filaments of these polymers with their many desirable chemical and physical properties offer much in specific end uses; however, the art has not been able to develop a satisfactory fire retardant additive, or additives, for polyolefins. In selecting such an additive, care must be taken that the additive does not alter the properties of the resin, e.g., color, flexibility, tensile strength, electrical properties, softening point, etc.; however, to date, the art has been unable to develop a suitable system which will impart fire retardancy to poly-α-olefins without unsatisfactorily affecting some of the desirable properties of the resin.

More specifically directed to the present invention, the synthetic textile industry was desirous of obtaining a fire retardant polyolefin fabric, wherein the presence of the fire retardant on or in the fabric would in one respect be effective as a flame retardant while in another respect would not alter the desirable properties of the fabric, particularly, the hand.

The prior art sought to incorporate certain phosphates into the thermoplastic melt in an attempt to provide an inherent flame retardant polypropylene. In Listner, U.S. Pat. No. 3,650,300, granted Mar. 21, 1972, polyolefins were rendered flame retardant by the incorporation of an antioxidant, a halogen phosphate, a free radical initiator and a dispersant into the thermoplastic melt. In Murray et al, U.S. Pat. No. 3,663,502, granted May 16, 1972 phosphine oxides and ammonium polyphosphates were incorporated into the polypropylene melt or mix. In Versnel, U.S. Pat. No. 3,893,970 granted July 8, 1975, a phosphite adjuvant is incorporated into molten polypropylene. In Wolf I U.S. Pat. No. 3,894,876, granted July 15, 1975 and Wolf II, U.S. Pat. No. 3,894,121 granted July 8, 1975, phosphonitrilic esters are considered for flame proofing synthetic materials. In Nachbur et al, U.S. Pat. No. 3,800,010, granted Mar. 26, 1974, phosphonopropionic acid amines are proposed as flame proofing agents for fibers or in plastics.

In Goldborn et al I, U.S. Pat. No. 3,803,269 granted Apr. 9, 1974, Goldborn et al II, U.S. Pat. No. 3,870,771 granted Mar. 11, 1975, Goldborn et al III, U.S. Pat. No. 3,935,162, and Goldborn et al IV, U.S. Pat. No. 3,976,620, various alkyl-aryl phosphonates were proposed for incorporation into polyolefin thermoplastic melts to provide flame retardancy.

In Anderson et al I, U.S. Pat. No. 3,849,368 granted Nov. 19, 1974 and Anderson et al II, U.S. Pat. No. 3,789,091 granted Jan. 29, 1974 certain cyclic phosphonate esters were proposed to be incorporated into polyesters to provide flame retardancy. Polyolefins and polypropylene substrates are not mentioned.

While such prior art compositions provided flame retardancy, the compositions were necessarily compounded by the resin manufacturers and could not be practically employed by synthetic textile fabricators, and more specifically by those utilizing polyolefin textiles for matting and fabric coverings. That is to say the commercial manufacturer of polyolefin wall coverings could neither control the level of the flame retardancy nor the quality of the product. This was a particular problem in that the aforesaid prior art flame retardant polyolefins when fabricated as a textile had an undesirable or unacceptable hand.

Now there is provided by the present invention a composition and method for rendering polyolefin textile materials flame retardant without loss of the desirable textile properties such as a good hand.

It is therefore an object of this invention to provide a flame retardant polyolefin textile which exhibits desirable textile properties.

It is another object of this invention to provide a flame retardant composition and method for polyolefins.

It is still another object of this invention to provide a composition and method for flame retarding polyolefin textiles which can readily be used by synthetic textile product fabricators in contradistinction to resin manufacturers.

It is still a further object of this invention to provide a flame retardant polyolefin which retains its properties of flame retardancy and textile properties upon exposure to ambient environments.

It is still a further object of this invention to provide a polyolefin wall covering which meets the stringent requirements of regulatory flame retardancy tests.

It is still another object of this invention to provide a composition and method for flame retardant polyolefins which is commercially useful, and yet safe and practical in operation.

DESCRIPTION OF THE PREFERRED EMBODIMENTS

Broadly speaking, in one aspect, the flame retardant composition of the present invention comprises;

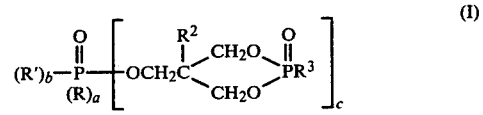
(I)

wherein a is 0, 1 or 2, b is 0, 1 or 2, c is 1, 2 or 3 and a+b+c is 3; R and R' are the same or dissimilar and are alkyl, alkoxy, aryl, aryloxy, alkaryl, alkaryloxy, aralkyl, aryloyxalkoxy, or aralkoxy wherein the alkyl portion of these groups may contain hydroxyl but no halogen and the aryl portion may contain chlorine bromine and hydroxyl groups; $R^2$ is alkyl, hydroxyalkyl, or aryl; $R^3$ is lower alkyl ($C_1$–$C_4$); and a wetting agent penetrant. The presence of the penetrant promotes penetration of the retardant composition into the polypropylene.

The compound of formula I in combination with the penetrant when coated onto the surface of the polyolefin provides excellent flame retardant properties to the polyolefin.

In a more specific aspect the composition of the present invention comprises;

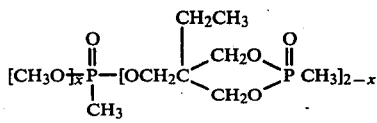

(II)

wherein x is 0 or 1; and a polyolefin wetting agent comprising a polar radical and a non-polar radical, and wherein the composition is in aqueous solution.

The utilization of an aqueous system now permits textile fabric works to pass polyolefin fabrics through an aqueous bath at controlled parameters to effect pickup of the aforesaid flame retardant compositions.

Compounds of formulae I and II are generally disclosed in Anderson I, U.S. Pat. No. 3,849,368, and Anderson II, U.S. Pat. No. 3,789,091 and are commercially available from Mobil Oil Corporation, New York, N.Y.

Desirably the compound of formula II should have the following properties pursuant to the present invention.

| Active Ingredient | 50% in water |
|---|---|
| Appearance | Clear Liquid |
| Phosphorus (% by wt.) | 11.0 |
| Specific Gravity | 1.20 |
| Flash Point at 240° C. | 464° F. |
| pH | 3.0 |
| Solubility (grams/100cc) | |
| Water | Miscible |
| Acetone | Miscible |
| Ethanol | Miscible |
| Pentane | <5 |
| Benzene | >10 |
| Ethylene Chloride | >10 |

Suitable penetrants or wetting agents are generally those compounds which have both polar and non-polar radicals when in aqueous media. Examples of such are organic alcohols, and sols (e.g. butanol, butyl cellusol), or organic esters.

Certain organic esters when dissolved in water provide the desirable penetrating properties. Suitable organic esters include by way of example, phosphate ester, phosphonic acid esters, carboxylic acid esters and sulfonic acid esters. Most preferred are the phosphate esters, with lower alkyls $C_1$ to $C_4$.

Suitable esters of phosphonic acids have the structure:

(III)

wherein R, R' and R''' are methyl, ethyl, propyl, butyl, octyl, phenyl, halophenyl, hydroxyphenyl, tolyl, xylyl, benzyl, phenethyl, hydroxyethyl, phenoxyethyl, dibromophenoxyethyl, with the proviso that either R' or R'' is methyl, ethyl, propyl, butyl or hydroxyalkyl ($C_1$–$C_4$).

Suitable esters of phosphoric acids have the structure:

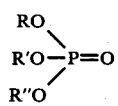

(IV)

Operative examples are those where R, R' and R'' are same as defined for the phosphonic acids hereinabove with the proviso that at least one R, R' or R'' group is methyl, ethyl, propyl, butyl or hydroxyethyl.

Suitable esters of carboxylic acids have the structure:

(V)

where x is 1–3 and Z is a monovalent radical such as methyl, ethyl, propyl, butyl, hexyl, phenyl, chlorophenyl, bromophenyl, dibromophenyl, tribromophenyl, hydroxyphenyl, naphthl, tolyl, xylyl, benzyl, or phenethyl; or Z is a divalent radical such as methylene, ethylene, hexylene, and the like.

Diesters of alkylene glycols such as ethylene glycol diacetate are also contemplated.

Suitable esters of sulfonic acid have the structure:

(VI)

Operative samples are those where R is defined as for the phosphonic acids above and R' is methyl, ethyl, propyl, butyl and hydroxyalkyl ($C_2$–$C_4$).

It is most preferred that in formulae III–VI, that R, R', R'' and R''' be the lower alkyls (e.g. $C_1$–$C_4$).

The compounds of formulae I and II are dissolved in water to the extent that between about 25 percent and 75 percent by weight of the compound is in solution; and the penetrant is present in amounts of from about 0.5 to 10 percent by weight of the solution, and preferably 1 to 5 percent.

Preferably the formula II compound is present in 50% by weight and the penetrant is present as 1 percent by weight solution.

It has been found in the practice of this invention that whereas in the prior art, relatively large percentages of up to 25 percent by weight of the flame retardant had to be incorporated into the polymer structure, that only about 5 to 15 percent by weight of the present composition be incorporated onto the polyolefin structure to achieve the desired flame retardation. At 8 percent by weight (dry) of the composition of the present invention into a polypropylene fabric, the optimum ratio of flame retardancy to minimum utilization of composition is achieved, with retention of a good hand.

Without wishing to be bound by any theory or mechanism it is proposed that one novel effect of the present invention is that the presence of the flame retardant on the surface of and to some degree below the surface of polypropylene fabric (by virtue of the penetrant) permits an ambient moisture retention of about 3 to 4 percent, whereas neat polypropylene fabric retains only about 0.3 percent by weight of ambient moisture. It is suggested that in this aspect, this higher moisture content aids in the level of fire retardancy for relatively low weight percentages of retardant retained in the fabric.

Suitable polymers useful pursuant to the present invention include the polyolefins, such as polymers of the monomers; ethylene, propylene, butene, pentene, hexene, heptene, octene, 2-methylpropene-1, 3-methylbutene-1, 4-methylpentene-1, 4-methylhexene-1, 5-methylhexene-1, bicyclo-(2.2.1)-2-heptene, butadiene, pentadiene, hexadiene, isoprene, 2,3-dimethylbutadiene-1,3,2-methylpentadiene-1,3,4-vinylcyclohexene, vinylcyclohexene, cyclopentadiene, styrene and methylstyrene, and the like.

The polymers of the invention can be in various physical forms, such as shaped articles, for example, moldings, sheets, rods, and the like; fibers, coatings, films and fabrics, and the like. Most preferred is wherein the polyolefin is shaped as a fabric.

In a preferred aspect of this invention, the polyolefin is a polypropylene fabric which may in a most preferred aspect be backed with a thermoplastic material. Suitable thermoplastic backings include the homopolymers and copolymers of aliphatic, alicyclic and aromatic hydrocarbons, and particularly polyesters.

Most suitable thermoplastic backing include polymers of acrylate esters and polymers of methacrylate esters, acrylate and methacrylite resins such as ethyl acrylate, n-buthyl methacrylate, isobutyl methacrylate, ethyl methacrylate and methyl methacrylite; polyester elastomers; vinyl resins such as polymer of vinyl acetal, vinyl acetate, vinyl chloride, vinyl butyral, and the like.

The preferred backings are butylacrylate/ethyl acrylate copolymer and acrylic copolymers.

The thermoplastic backing is coated with the retardant of formulae I and II at any desirable or useful concentration.

In the practice of this invention, a aqueous bath comprising 50 percent by weight of formula II compounds and 1 percent by weight of a penetrant is prepared and the bath is maintained at 100° F. Make-up bath was provided wherein the formula II compounds were present in 18 to 35 percent by weight and the penetrant is 1 to 5 percent by weight. A continuous web of neat polypropylene fabric is passed through the bath so as to achieve at wet pick-up of from 75 to 125 percent by weight of the solution, and preferably between 100 and 125 percent. The wet fabric is then continuously passed through a mangle so as to extract the latent solution. Then the fabric is continuously passed through a continuous air circulated oven maintained at about 320° F., but not in excess of about 400° F. It is important that the fabric temperature itself not exceed 260° F. The oven drying is controlled so that there is between 2 and 5 percent moisture in the fabric at the end of the oven dry and tenter frame extension of the fabric.

The following examples are illustrative of the invention:

EXAMPLE I

Two samples were prepared in general accordance with the aforesaid procedure, said samples were woven Herculon ("Herculon" is a registered trademark of Hercules Chemical Co., Wilmington, Del.) polypropylene having however the following retardant compositions:

|  | Sample A | Sample B |
|---|---|---|
| Retardant | 15% Formula II phosphonate esters[1.] | 15% Formula II Phosphonate esters[1.] |
| Hand Modifier | 5% GloRez CLFR[2.] | 5% GloRez CLFR[2.] |
| Penetrant | .2% Butyl Cellu-Sol[3.] | .2% Butyl Cellulose |

Sample B differed from Sample A in that Sample B was acrylic back-coated, with a coat of the of formula II phosphate esters, as above.

Both samples in swatches of 5 in. ×3 in. were subjected to a flame at one edge (lengthwise). Both samples showed no after-flame and therefore are self-extinguishing. Sample A exhibited a 3.5 inch char whereas Sample B exhibited a 3.0 inch char, during identical flame presence periods.

EXAMPLE II

Several polyolefin[4.] fabric samples treated in the manner as aforesaid, and having the following compositions:

| Formula II phosphonate esters[1.] | 8–9% by weight |
|---|---|
| Penetrant (Butyl-CelluSol[2.]) | 0.2% by weight | were tested according to Ordinance of 1959, Chapter 3, Document No. 34 of the City of Boston Fire Prevent-in Code[5.], and the results are reported in Table I.

TABLE I

|  | Afterflame (Seconds) | Burning of Drippings (Seconds) | Afterglow (Seconds) |
|---|---|---|---|
| Length |  |  |  |
| Test 1 | 0.0 | 0.0 | 0.0 |
| Test 2 | 0.0 | 0.0 | 0.0 |
| Test 3 | 0.0 | 0.0 | 0.0 |
| Width |  |  |  |
| Test 1 | 0.0 | 0.0 | 0.0 |
| Test 2 | 0.0 | 0.0 | 0.0 |
| Test 3 | 0.0 | 0.0 | 0.0 |

[1.] Anti-Blaze 19 (Mobil Oil Corp., New York, N.Y.)
[2.] (Glotex Chemical Co., Roebuck, S.C.) - acrylic emulsion
[3.] butylated Sol. (Union Carbide Corp., New York, N.Y.)
[4.] Herculon product
[5.] See "Textile Flammability - A Handbook of Regulation, Standards, and Test Methods" of the American Association of Textile Chemists and Colorists, pp. 201–204.

What is claimed is:

1. A flame retardant for a polyolefin comprising in combination in aqueous media;

a phosphonate ester having the following formula:

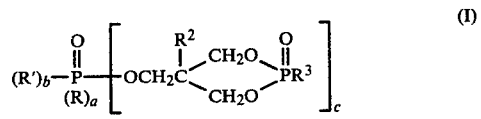

wherein a is 0, 1 or 2, b is 0, 1 or 2, c is 1, 2 or 3 and a+b+c is 3; R and R' are the same or dissimilar and are alkyl, alkoxy, aryl, aryloxy, alkaryl, alkaryloxy, aralkyl, aryloxy-alkoxy, or aralkoxy, wherein the alkyl portion of these groups may contain hydroxyl but no halogen and the aryl portion may contain chlorine, bromine and hydroxyl groups; $R^2$ is alkyl, hydroxyalkyl, or aryl; $R^3$ is lower alkyl ($C_1$–$CH_4$); and a penetrant for the ester, said penetrant is a phosphate ester, and said phosphonate ester and phosphate ester being in aqueous solution, and whereby the penetrant and phosphonate ester penetrate from the aqueous medium into the polyolefin below the surface thereof.

2. The flame retardant of claim 1, said penetrant comprises both polar and non-polar radicals in said aqueous medium.

3. The flame retardant of claim 1, wherein the phosphate ester comprises lower alkyl groups.

4. The flame retardant of claim 1, wherein the phosphonate ester is present in about 25 to 75 percent by weight of solution and the penetrant is present in about 1 to 10 percent by weight.
5. The flame retardant of claim 1, wherein the phosphonate ester has the following formula:
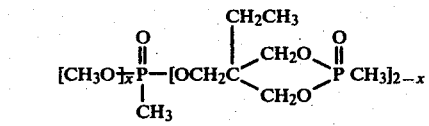
wherein x is 0 or 1.
* * * * *